United States Patent [19]  
Shimomura et al.

[11] Patent Number: 4,507,194  
[45] Date of Patent: Mar. 26, 1985

[54] REFERENCE ELECTRODE

[75] Inventors: Takeshi Shimomura; Shuichiro Yamaguchi, both of Kawasaki; Norihiko Ushizawa, Honmachi; Noboru Oyama, Higashikurume, all of Japan

[73] Assignee: Terumo Kabushiki Kaisha, Tokyo, Japan

[21] Appl. No.: 518,354

[22] Filed: Jul. 29, 1983

[30] Foreign Application Priority Data

Aug. 2, 1982 [JP] Japan ............................... 57-134883

[51] Int. Cl.$^3$ ............................................ G01N 27/30
[52] U.S. Cl. .................................................... 204/435
[58] Field of Search ................... 204/435, 418, 290 R, 204/291

[56] References Cited

U.S. PATENT DOCUMENTS 3,490,440  1/1970  Mosier et al. ....................... 128/639
3,662,745  5/1972  Consentino ..................... 204/435 X
3,856,649  12/1974 Genshaw et al. ............... 204/435 X
4,214,968  7/1980  Battaglia et al. ................ 204/435 X
4,263,343  4/1981  Kim ................................. 204/435 X
4,282,079  8/1981  Chang et al. .................... 204/435 X

OTHER PUBLICATIONS

*Journal of The Electrochemical Society*, vol. 127, No. 5, May 1980, "Polymer-Metal Composite Thin Films On Electrodes", K. Doblhofer et al., pp. 1041-1044.
Soviet Inventions Illustrated, Week C 02, Feb. 20, 1980, Sections JO4, A89, R16 (SU-A-658 459, published 1/31/75).
Patent Abstracts of Japan, vol. 5, No. 36, Mar. 7, 1981, (JP-A-55-1158552 published 12/10/80).

*Primary Examiner*—G. L. Kaplan  
*Assistant Examiner*—Nam X. Nguyen  
*Attorney, Agent, or Firm*—Frishauf, Holtz, Goodman & Woodward

[57] ABSTRACT

A reference electrode is prepared by coating the surface of a conductive substrate with a silver complex polymer compound, which is either a compound prepared by the complex formation between a polymer compound containing a coordination nitrogen atom and a silver ion or an aforementioned complex compound containing a silver halide. This reference electrode can be used by a combination with ion sensor, a pH sensor and so on.

14 Claims, 10 Drawing Figures

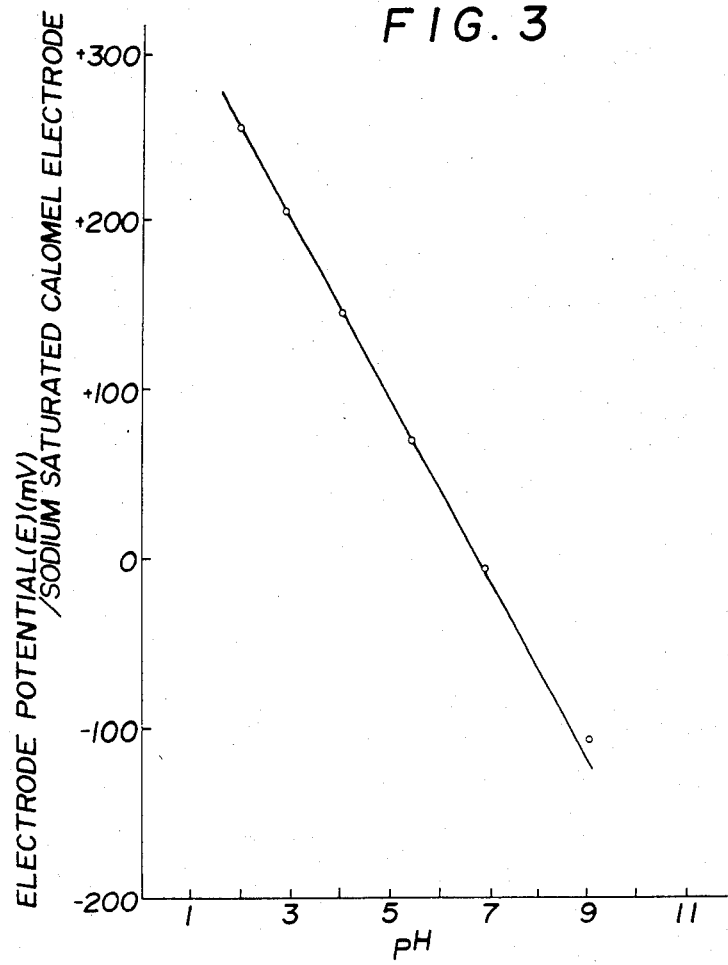

REFERENCE ELECTRODE

BACKGROUND OF THE INVENTION

1. Field of the Invention

This invention relates to a reference electrode. Particularly this invention relates to a reference electrode which features simplicity of construction, permits miniaturization, and possesses an insensitive film on its electrode surfaces. More particularly, this invention relates to a reference electrode used by a combination with an ion sensor, a pH sensor and so on.

2. Description of Prior Arts

In recent years, the coating on the surface of a conductor with a film for the purpose of conferring a new potentiality upon the conductor has come to prevail. The electrode coated with such a film is generally called a "polymer coated electrode." The polymer coated electrode shows a promise in potential application to electrocatalysis, transducers, analytical sensors and so on. To exploit such a novel function, the polymer coated electrode dictates payment of due consideration to electroconductivity and other various properties to be displayed by the coating film directly applied to the surface of the electrode. In the case of an electrode to be used for an ion sensor or a pH sensor, for example, the coating film is required to possess selective permeability to a particular ion species desired to be detected.

Heretofore, a saturated calomel electrode and a silver/silver chloride electrode have been chiefly used as a reference electrode.

A reference electrode is required to possess a room for holding the saturated sodium chloride (NaCl) solution into which $Hg/Hg_2Cl_2$ or $Ag/AgCl$ is dipped. The reference solution of the saturated NaCl and a test solution is connected each other across a thin glass filter. When such a reference electrode is to be miniaturized or to be used in the field of medical inspection, since the reference electrode is furnished a room of reference solution, there is the possibility that a test solution under measurement mingles with the reference solution or the inner reference solution leaks owing to change in the temperature of the solution under measurement. Besides, the reference solution itself becomes a serious obstacle to fabricate the electrode in a miniaturized design. Thus, various difficulties are inevitably encountered. As a solution of these problems occuring from a reference solution, we have filed Japanese Patent Application No. 206095/1981, covering an invention relating to a reference electrode having at least one polymer film (a film of the polymer derived from a hydroxyaromatic compound) directly coated either on the surface of a conductor (chiefly of silver) or on the surface of a layer of a halide (chiefly silver halide) deposited on a conductor. Since this reference electrode has been prepared simply by coating the surface of a conductor with a polymer film, it does not require incorporation of any room of a reference solution and can be miniaturized to the limit imposed only by the fabricability of the conductor. In general, the deposition of the polymer film on the conductor is effected chiefly by the electrochemical oxidation polymerization technique, enabling the surface of the conductor to be directly coated with the film.

SUMMARY OF THE INVENTION

An object of this invention, therefore, is to provide a novel reference electrode.

Another object of this invention is to provide a reference electrode which features simplicity of construction, permits miniaturization, and possesses an insensitive film on the surface of a conductor.

These and other objects of this invention are accomplished by a reference electrode, produced by depositing on the surface of a conductor a polymeric silver complex which is formed either by complex formation between a polymer compound containing a coordination nitrogen atom and a silver ion or a mixture of the aforementioned complex compound with a silver halide.

In accordance with this invention, there is provided a reference electrode which is produced by depositing a polymeric silver complex on the surface of a conductor.

The conductive substrate has at least the surface of silver or a silver halide on the conductor.

Examples of the polymer compound containing a coordination nitrogen atom include polyacrylamide, polymethacrylamide, polyvinylamine, polyacrylonitrile and polymethacrylonitrile.

The coating of the film on a conductor is effected chiefly by the electrochemical oxidation polymerization of monomer. However, in the case of the conductor of silver, silver is also oxidized and dissolved in a solution at the electrochemical polymerization potential of monomer. Therefore, at first the coating on the surface of silver is mainly performed by the dip coating method. Then, silver ion is dissolved in the foregoing layers of the polymer having a coordination nitrogen atom by the electrochemical oxidation of silver and the resulting film on the surface of silver becomes the film of the polymer silver complexes.

The aforementioned layer of a polymer complex compound can be coated further with a film capable of precluding penetration of obstructive ions as occasion demands. Generally, the film for precluding penetration of obstructive ions is formed with a poly(hydroxyaromatic compound), polypropylene, a poly(organic fluorine compound), polyvinylidene chloride, polycarbonate, silicone resin, epoxy resin or a polyelectrolyte.

BRIEF DESCRIPTION OF THE DRAWING

FIG. 2 through FIG. 9 are each a graph showing characteristics of the reference electrode of this invention.

PREFERRED EMBODIMENT OF THE INVENTION

Now, the present invention will be described in detail below with reference to the accompanying drawing.

Figure 1:
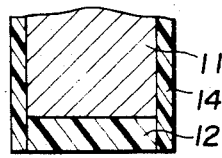
FIG. 1(A) and FIG. 1(B) are partial enlarged sections of reference electrodes according to this invention.
Figure 1:
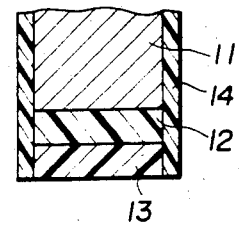

The reference electrode of this invention comprises, as illustrated in FIG. 1(A), a conductive substrate 11 and a layer 12 prepared by complex formation between a polymer compound containing a coordination nitrogen atom and a silver ion. The conductor 11 is desired to have at least the surface formed with silver. The surface will consist either solely of silver or a thin layer of silver deposited on some other conductor by using a spattering device.

For the purpose of coating the polymeric silver complex layer 12 on the surface of the substrate 11 having at least the surface of with silver, the electrochemical oxidation technique can be advantageously adopted. The surface of the substrate 11 is first smoothened by polishing, washed with water, cleaned with methanol, and then dried. In the subsequent electrolysis, there is used an ordinary three-electrode type cell, using the substrate under the treatment as a working electrode, a platinum wire as a counter electrode, and a sodium chloride-saturated calomel electrode as a reference electrode. The electrolyte to be used for this electrolysis is prepared by adding a supporting electrolyte to a solution of a polymer having a coordination nitrogen atom. When the substrate is electrolyzed, silver ion is dissolved from the surface layer of the substrate by the oxidation and the silver ion thus dissolved forms a silver complex compound with the polymer compound in the electrolyte and, consequently, the silver complex compound becomes insoluble and is deposited in the form of a layer on the surface of silver. In this case, the formation of a layer of polymeric silver complex compound is recognized by a reddish brown color change of the surface of conductor. This layer of the complex compound is a viscous film. Thus, the tenacious layer of the polymeric silver complex compound 12 is formed on the surface of the conductor 11.

This layer of polymeric silver complex compound has a thickness in the range of $10^{-2}$ to $10^4$ μm preferably $10^1$ to $10^3$ μm.

The polymer compound containing nitrogen atom capable of being bonded by coordination with the silver ion is a linear polymer having repeating units of the general formula (I):

wherein R denotes hydrogen atom, an alkyl group having 1 to 6 carbon atoms or an alkoxy group having 1 to 6 carbon atoms and x denotes $CONH_2$, $CN$ or $NH_2$. Concrete examples of the polymer compound containing a coordination nitrogen atom are polyacrylamide, polymethacrylamide, polyvinylamine, polyacrylonitrile and polymethacrylonitrile. The average molecular weight of this polymer is in the range of $10^3$ to $10^6$, preferably $10^4$ to $10^6$.

The formation of the polymeric silver complex layer 12 may be otherwise effected by adding silver nitrate, for example, to the solution of the aforementioned polymer compound thereby giving rise to a complex formation in the solution, coating the resultant complex-containing solution to the surface of the conductor 11, and drying the coated solution.

The polymeric silver complex layer may contain therein a silver halide (e.g., silver chloride). The surface of a silver conductor 11 can be coated with a silver halide. The incorporation of the silver halide into the aforementioned layer of the polymeric silver complex is accomplished by adding the silver halide (e.g., silver chloride) to the solution containing the aforementioned polymeric silver complex.

The formation of the layer of a silver halide on the surface of the silver conductor is performed by treating the surface of silver with a halogen gas (e.g., chlorine gas). On the layer of the silver halide consequently obtained, the polymeric silver complex layer is coated by the aforementioned coating method. Alternatively, by carrying out an electrochemical oxidation in an electrolyte containing sodium chloride as a supporting electrolyte, a polymeric silver complex layer containing silver chloride can be formed on the conductor. Optionally, the substrate 11 can be prepared with a conductive adhesive agent containing silver. Otherwise, the reference electrode can be obtained by binding the polymeric silver complex or a mixture thereof with a silver halide in the form of a film on the surface of the conductor with the aid of an adhesive agent (such as, for example, epoxy type resin). It is further permissible to have an ion-permeating film to be interposed between the surface of the conductive substrate 11 and the polymeric silver complex layer. Examples of the ion-permeating film useful in this case include cellulose type resin film, hydroxyaromatic compound type polymer or vinyl type polymer (inclusive of a cross-linked type polymer).

When the reference electrode in any of the embodiments described above is used in a test solution wherein an obstructive ion species is present in a concentration high enough affect the magnitude of the equilibrium potential of the reference electrode, it is desirable to coat the layer of the polymeric silver complex with at least one more layer of a film (porous film) formed of a poly(hydroxy-aromatic compound), a poly(nitrogen-containing aromatic compound), polypropylene, a poly-(organic fluorine compound), polyvinylidene chloride, polycarbonate, silicone, epoxy resin or polyelectrolyte [which film is indicated by 13 in FIG. 1(B)] for precluding penetration of obstructive ion. Particularly in the case of a reference electrode which uses the polymeric silver complex containing silver chloride or possesses a silver chloride layer on the surface of the conductor, it is desirable to use a polymer film containing chloride ion such as, for example, a film of polyvinyl pyridine quaternized with methyl chloride (e.g., polyvinyl pyridine of an average molecular weight of 7200 quaternized to 90% of degree of quaternization with methyl chloride; hereinafter referred to as QPVP) in order to preclude penetration of an obstructive ion and fix chloride ion strongly in the film of the polymeric silver complex. In this case, the reference electrode shows a constant value of equilibrium potential stably over a wide pH range (pH 3.0 to 10.0) because the QPVP permits relatively stable presence of chloride ion therein.

The insulating layer 14 of reference electrode is formed with insulating agent such as tetrafluoroethylene resin.

The nitrogen-containing aromatic compound to be used for the formation of the aforementioned polymer of nitrogen-containing aromatic compound may be a compound of the general formula II:

wherein Ar denotes an aromatic ring, R a substituent, m either 0 or an integer having the value of at least 1, n an integer having the value of at least 1, providing that the sum of m+n does not exceed the number of the available valency of Ar and that n may be O when Ar is a nitrogen-containing heterocycle. The aromatic ring, Ar, may be of the monocyclic form (such as, for example, benzene ring or pridine ring) or the polycyclic form (such as, for example, quinoline ring, naphthoquinone ring, or bisphenol ring). An N-substitution derivative of the compound of the general formula II may be also usable.

Examples of the substituent R are alkyl groups such as methyl group, halogenated alkyl groups, aryl groups such as phenyl group, alkylcarbonyl groups, arylcarbonyl groups,

hydroxyalkyl groups (—R"OH), carboxyl group aldehyde group and hydroxyl group.

Concrete examples of the nitrogen-containing aromatic compound include, 1,2-diaminobenzene, aniline, 2-aminobenzotrifluoride, 2-aminopyridine, 2,3-diaminopyridine, 4,4'-diamino-diphenyl ether, 4,4'-methylene dianiline, tyramine, N-(0-hydroxybenzyl)-aniline and pyrrole. Examples of the polymer obtained in advance by polymerization include polyaromatic amides and imides such as polyamide-imide compounds of 4,4'-diaminodiphenyl ether and 4,4'-diaminodiphenyl methane derivatives and the polyamide polymer which is obtained by converting bis-cyclo-[2,2,2]-oct-7-ene-2,3,5,6-tetracarboxylic acid dianhydride into an acid chloride through reaction with thionyl chloride and causing the resultant acid chloride to react with 4,4'-diaminodiphenyl ether [as reported by Kobayashi et al. in Journal of Japan Chemical Society, (12), pp 1929–1932 (1980)].

The hydroxy-aromatic compound to be used for the formation of the aforementioned poly(hydroxy-aromatic compound) may be represented by the general formula (III):

wherein Ar denotes an aromatic ring, R a substituent, and l either 0 or the number of the available valency of Ar. The aromatic ring, Ar, may be of the monocyclic form (such as, for example, benzene ring or pyridine ring) or the polycyclic form (such as, for example, quinoline ring, naphthoquinone ring or bis-phenol ring). The substituent R is the same as that which was described formerly with respect to the general formula (II).

Concrete examples of the hydroxy-aromatic compound used in the foregoing description include phenol, dimethyl phenols (such as, for example, 2,6- and 3,5-dimethyl phenols), 2-, 3- and 4-hydroxypyridines, o- and m-benzyl alcohols, o-, m- and p-hydroxybenzaldehydes, o-, m- and p-hydroxyacetophenones, o-, m- and p-hydroxypropiophenones, o-, m- and p-benzophenols, o-, m- and p-hydroxybenzophenols, o-, m- and p-carboxyphenols, diphenylphenols (such as, for example, 2,6- and 3,5-diphenylphenols), 2-methyl-8-hydroquinoline, 5-hydroxy-1,4-naphthoquinone, 4-(p-hydroxyphenyl)-2-butanone, 1,5-dihydroxy-1,2,3,4-tetrahydronaphthalene and bisphenol A. Examples of the polymer obtained in advance by polymerization include polyphenylene oxide, polyphenylene oxide derivatives, polydiphenyl phenylene oxide, polydimethylphenylene oxide and polycarbonate.

In order to coat the polymer film of the aforementioned nitrogen-containing aromatic compound or hydroxy-aromatic compound on the surface of the polymeric silver complex layer 12 the following method can be used; a method which comprises depositing the nitrogen containing aromatic compound or hydroxy-aromatic compound on the surface of the layer 12 by the electrochemical oxidation polymerization of the corresponding monomer, a method which comprises coating the preliminarily synthetized polymer solution on the surface of the conductor and drying the applied layer, or a method which deposits directly a polymer film on the layer 12 by a physical treatment, or a treatment with radiation.

EXAMPLE 1

The surface of a thin copper film on a print substrate made of glass fiber-reinforced epoxy resin was polished with silicon carbide paper and alumina powder (0.3 μm in diameter), washed with water and with methanol and dried. This surface of the copper film was covered with silver thin film by a two-electrode magnetron spattering device (ANELVA model SPF-210H). Then, a copper leading wire was connected to the remainder of the exposed copper surface. The thickness of silver film was 0.020 μm under the experimental condition of the two-electrode magnetron spattering device: irradiation distance 40 mm, argon gas pressure 7 Pa, electric power 200 W, and irradiation time 20 sec.

The surface of the resulting silver film was coated with a thin film of a metal complex polymer, which consists of 0.1 ml/cm²-surface of 30 wt% aqueous solution of polyacrylamide containing 30 wt% silver nitrate and below 1 wt% silver chloride, and then the electrode obtained was coated with epoxy resin. The construction of the electrode is combined with silver/silver ion (incorporated with silver complex polymer film)/silver chloride/epoxy resin.

Figure 2:
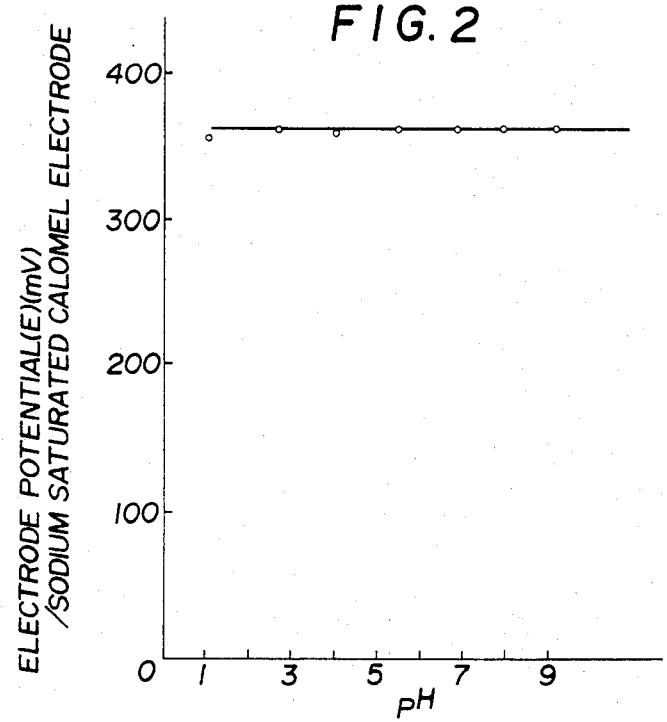

In order to elucidate the properties of the resulting electrode as a reference electrode, its electrode potential was measured against a commercially available sodium chloride-saturated calomel electrode (SSCE) (Toa Denpa HC-205C) in standard buffer solution of various pH values. The relation obtained between electrode potential and pH value was shown in FIG. 2, where pH value was determined by a commercially available glass electrode. In a pH range between 4.0 and 10.0, the electrode potential was constant (362±2 mV vs. SSCE), indicating that the electrode of this invention could serve as a reference electrode. The response time of the electrode was rapid, and the electrode potential reached its constant level within 30 seconds.

The reference electrode of this invention was used to measure the pH value in the standard buffer solutions mentioned above, where the platinum wire electrode coated with the film resulting from the electrochemical polymerization of phenol (its preparation procedure is mentioned below) was used as a working electrode. In a pH range between 2.0 and 10.0, the relation between the electrode potential and the pH value was found to be linear (FIG. 3). The gradient of the straight line was 54 mV/pH at 25° C., representing that the potential-pH relation obtained obeys the Nernst equation. The response time of the electrode was within 4 minutes. Thus, these experimental results indicate that the reference electrode of this invention can be used as a reference electrode for the measurement of pH.

The working electrode mentioned above was produced by the following procedure.

The electrolysis for the film formation on electrode surfaces was conducted by using the conventional electrolytic cell of H-type, which was equipped with a platinum gauze as an auxiliary electrode, a saturated calomel electrode as a reference electrode, and a platinum wire (1.0 mm in diameter) insulated with a sheath of tetrafluoroethylene resin as a working electrode. The surfaces of working electrodes were polished with alumina powder (diameter: 0.06 μm) to acquire smooth surface. After that, the surface were washed by dilute aqua regia and then by water. The electrolyte solution contained 10 m mol/l of phenol and 30 m mol/l of sodium hydroxide in methanol. It was thoroughly deaerated with an argon gas before the electrolysis. The potential was scanned to the anodic direction to confirm the occurrence of the oxidation reaction of phenol monomer on the surface of the platinum electrode. Then, the potential was held at 0.9 volt (vs. a saturated calomel electrode) for three minutes. Resultingly, the surface of the electrode was coated with the polymeric film produced from electrochemical polymerization of phenol. Thereafter, the surface of the electrode was washed three or more times with distilled water.

EXAMPLE 2

A silver wire (1 mm in diameter) was insulated with a sheath of tetrafluoroethylene resin. The exposed leading end of the sheathed silver wire was polished with a silicon carbide paper (about 8.0 μm in diameter) and alumina powder (0.3 μin diameter), washed with water, cleaned with methanol and then dried.

The silver electrode thus obtained was used as a working electrode in the electrolysis mentioned below, together with a platinum wire as an auxiliary electrode and, a commercially available SSCE (Toa Denpa HC 205C) as a reference electrode. The electrolytic solution used was an aqueous 3 weight percent polyacrylamide (of a molecular weight of about 500,000) solution containing sodium chloride or sodium perchlorate as supporting electrolyte. The potential was swept from 0.0 volt to 1.9 V (vs. SSCE) and then it was held at a constant potential of +1.9 V for three minutes. Consequently a dark brown layer of polymeric silver complex on the surface of the silver wire was formed.

Figure 4:
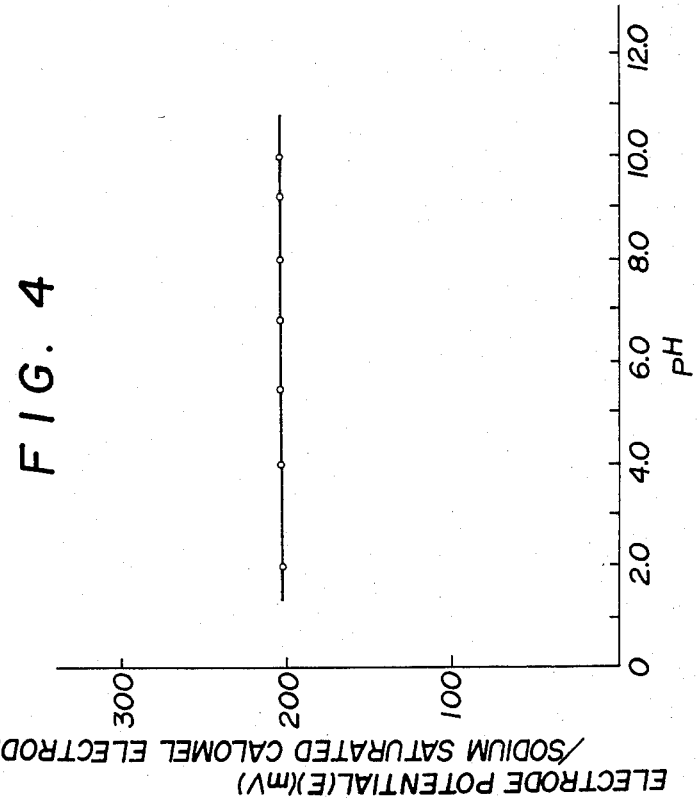

The characteristics of the electrode thus obtained as a reference electrode was examined in a wide pH range by following the procedure of Example 1. The relation of the hydrogen ion concentration and the electrode potential of a commercialy available glass electrode measured with respect to the electrode of this invention was linear in a pH range between 2.0 and 10.0, as can be expected from the Nernst equation. Further, as can be seen from FIG. 4, it became clear that the electrode potential of the electrode of this invention measured with respect to a commercially available SSCE was not affected by the hydrogen ion in the pH range from 2.0 to 10.0 and it's value was constant (206±2 mV vs. SSCE) at 25° C.

EXAMPLES 3 AND 4

As described in Example 2, a silver wire (1 mm in diameter) was coated with a sheath of tetrafluoroethylene resin. The leading end of the sheathed silver wire was smoothened by polishing, washed with water, cleaned with methanol, and then dried. By using the silver wire as an electrode and a dimethyl formamide 3 weight percent BAREX® (Vistron Co. trademark designation for a polyacrylonitrile (PAN) copolymer) solution as an electrolyte, the electrolysis was perfomed by scanning the potential several times in a range between −1.9 volts and +1.9 V (vs. SSCE) and, thereafter, by holding it at 1.9 V for five minutes. In this case, 0.1 mol/l tetrabutylammonium perchlorate (Bu$_4$NClO$_4$) solution was used as a supporting electrolyte. This reaction produced a reddish brown film of polymeric silver complex on the surface of the electrode. Then, this electrode was soak in a 0.2 weight percent tetrahydrofuran solution of SARAN® (Dow chemical trade mark: poly vinylidene chloride film) for one minute and then dried.

Figure 5:
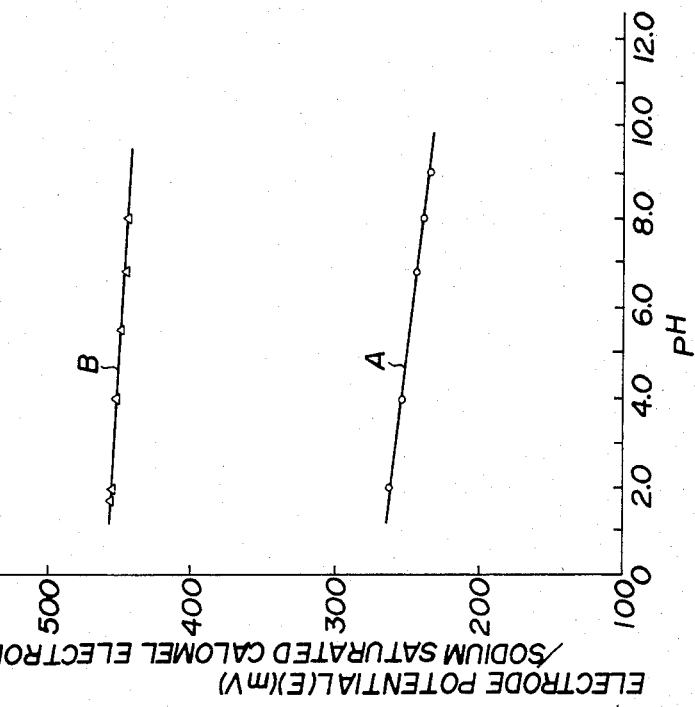

Thus, there was produced an electrode of a construction of silver base/polymeric silver complex/Saran film. This electrode was tested for performance of a reference electrode. The results were shown in Table 1 and FIG. 5 (line A). Separately, an electrode of a construction of [leading wire/copper base/silver film/polymeric metal complex (Ag(I)-PAN complex)/Saran film/porous film] was produced by adding silver nitrate (30 weight percent in concentration) to a dimethyl formamide solution containing 3 weight percent PAN thereby giving rise to a complex therein, casting the resultant solution on the surface of a thin silver film (the thickness of film on a copper substrate is about 0.02 μm) electrode, then directly depositing a Saran film (not more than about 10 μm in film thickness) swelled in a tetrahydrofuran solution onto it, and coating the Saran film with a porous film of epoxy resin.

This electrode was tested for performance of a reference electrode. The results were shown in Table 1 and FIG. 5 (line B). From these results, it is noted that the deposition of a porous film of epoxy resin on the Saran film enhanced the performane of the electrode as a reference electrode.

TABLE 1

| Example | Electrode construction | Effect of pH on value of equilibrium potential | pH range | Response time (time required to reach constant equilibrium potential |
| --- | --- | --- | --- | --- |
| 3 | Silver base/Ag(I)—Barex ® +/ Saran ® film | 4 mV/pH | 4.0–9.0 | about 5 minutes |
| 4 | Copper base/silver film/Ag(I)—PAN/ Saran ® film/porous film (epoxy resin) | 2 mV/pH | 2.0–8.0 | about 1 minute |

EXAMPLE 5

A silver wire (1 mm in diameter) was insulated with tetrafluoroethylene resin. The exposed leading end of the sheathed silver wire was smoothened by polishing, washed with water, cleaned with methanol and dried. This silver wire was exposed to chlorine gas for several minutes in order to the surface of silver wire with silver chloride. The solution containing Ag(I)-PAN complex, which was formed by adding silver nitrate to dimethyl formamide solution containing 3 wt% PAN, was applied to the surface of a silver-silver chloride electrode and then dried in order to form a siler-silver chloride electrode coated with a film of Ag(I)-PAN complex. Further, the surface of the electrode was coated with a Nafion film (obtained by dissolving polyfluorosulfonic acid resin, product No. 125 of E. I. duPont de Nemour & Co., to a concentration of 0.5 weight percent in dimethyl sulfoxide and applying 100 $\mu$l/cm$^2$ surface of the resultant solution onto the electrode surface). Then, the film of epoxy resin was deposited on this Nafion film. The resulting electrode was tested for performance as a reference electrode.

The effect of chloride ion upon the electrode potential (vs. SSCE) of the electrode of this invention was examined in a standard phosphate buffer solution (pH 4.01) containing sodium chloride, the concentration of which was varied between 0 and $10^{-1}$ mol/l. The results were shown in FIG. 6 (line A). The electrode potential remained constant (460 mV) without being affected by chloride ion in the concentration range of sodium chloride between 0 and $2\times10^{-2}$ mol/l.

EXAMPLE 6

Figure 6:
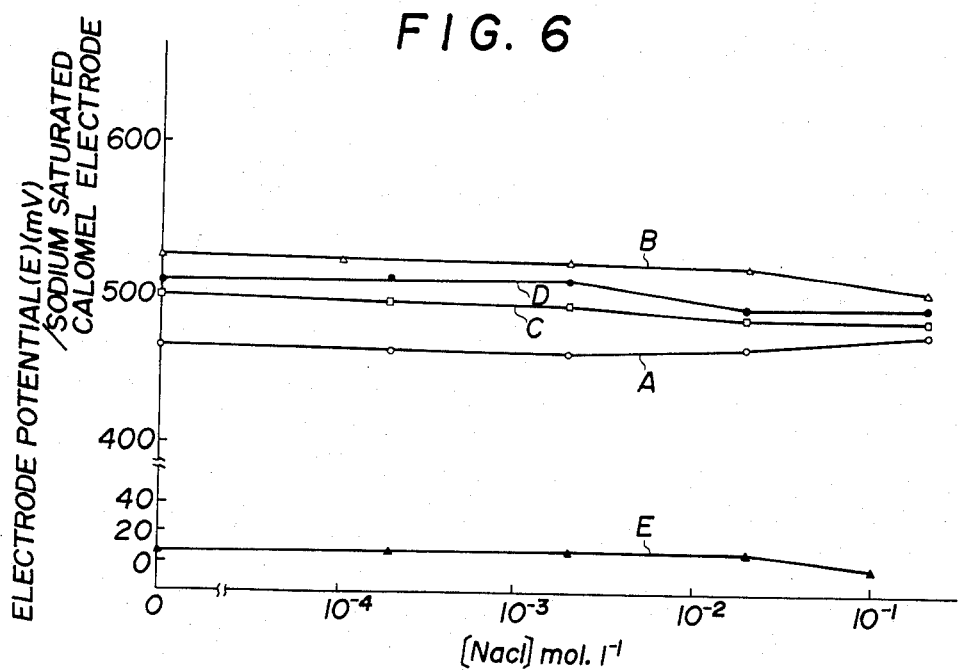
Figure 7:
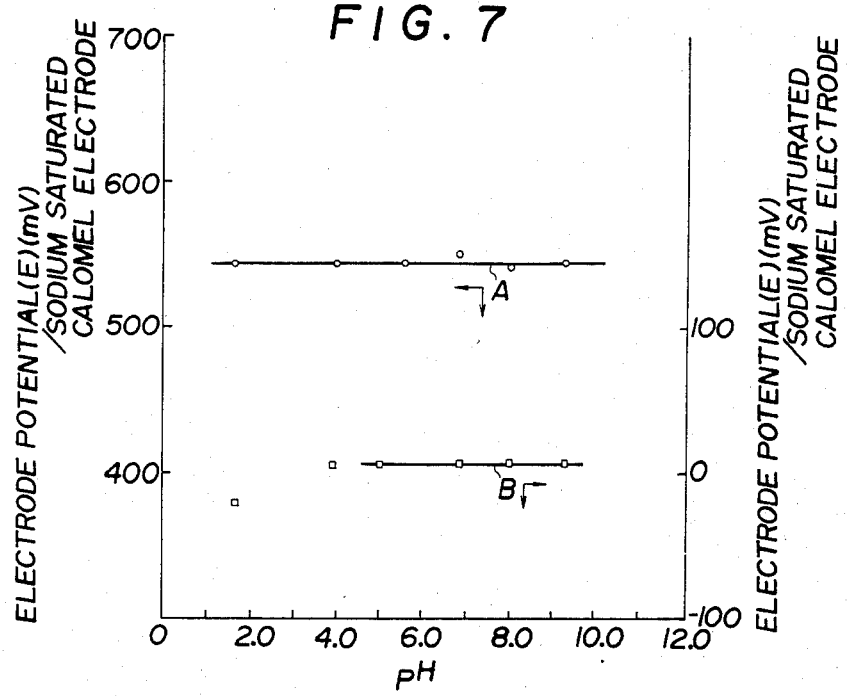

An electrode of the construction of [silver base (silver wire)/Ag(I)-PAN complex film/Nafion film/epxoy resin] was manufactured by coating a silver wire with a Ag(I)-PAN complex film by following the procedure of Example 4, further coating the complex film with a Nafion Ⓡ film by following the procedure of Example 5, and fixing the surface of the Nafion Ⓡ film with epoxy resin. This electrode was tested for performance as a reference electrode. The results were shown in FIG. 6(line B). As can be seen from these results, the electrode potential was constant (520 mV vs. SSCE) even when the test solution contained $1.0\times10^{-2}$ mol/l of chlorine ion. In the place of PAN, polyacrylamide (PAAm) was also used to construct the reference electrode under consideration. In this case, the effect of chloride ion upon the electrode potential was slightly observed as shown in FIG. 6(line C), where a standard phosphate buffer solution (pH 4.01) was used as a test solution. Further, it was observed that the electrode potential of the electrode of this invention was constant (542 mV vs SSCE) in the pH range between 2.0 and 10.0 (line A of FIG. 7).

EXAMPLE 7

By following the procedure of Example 4, an electrode of the construction of [silver base (silver wire)/silver chloride layer/Ag(I)-Pan complex layer/quaternized poly(vinyl pyridine):QPVP layer, Nafion Ⓡ film/epoxy resin layer] was prepared. This electrode was tested for performance as a reference electrode. The magnitude of electrode potential was constant (508 mV vs. SSCE) up to chloride ion of $2\times10^{-3}$ mol/l (line D of FIG. 6). In this test, a standard phosphate buffer (pH 4.01) solution was used as a test solution. In this case, the response time of the electrode was very rapid and the electrode potential reached the constant value within one minute.

To examine the effect of the Nafion film used in the construction of this electrode on its performance, there was separately prepared an electrode of the construction [silver wire base/silver chloride layer/QPVP layer/epoxy resin layer] which lacked a Nafion film. This electrode was similarly tested for characteristics as a reference electrode. The effect of the chloride ion upon the magnitude of electrode potntial was examined. The result was shown by line E of FIG. 6. The value of electrode potential remained constant (8 mV vs. SSCE) between 0 and $1\times10^{-2}$mol/l of chloride ion concentration. Furthermore, in this case, the electrode potential vs. SSCE was constant in a pH range between 4.0 and 9.0 (line B in FIG. 7), at 25° C.±0.1° C.

EXAMPLE 8

By following the procedure of Example 5 an electrode of the construction of [silver base (silver wire)/silver chloride layer/Ag(I)-PAN polymeric complex layer/QPVP layer/Nafion layer/epoxy resin layer] and an electrode of the aforementioned construction without a QPVP layer were prepared. These electrodes were tested for the characteristics as a reference electrode in a test solution containing a heavy metal ion and in a controlled serum solution.

Figure 8:
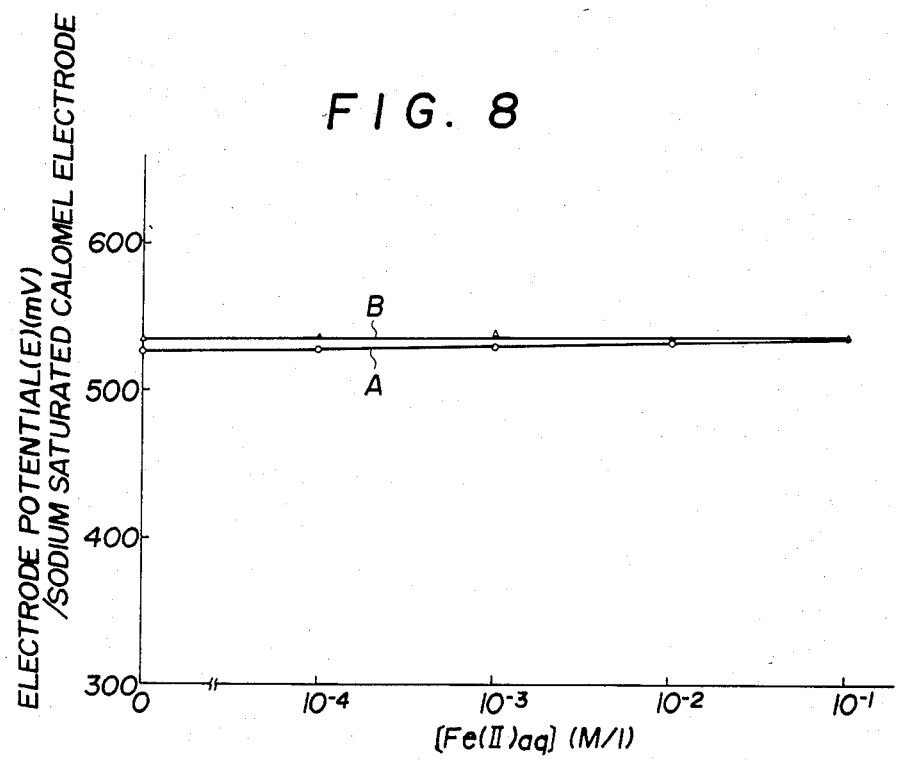

The effect of the iron (II) aqua ion upon the magnitude of the electrode potential of the electrode of this invention was examined in a standard buffer solution (pH 2.5 and 4.0), where the concentration of iron (II) ion was varied from 0 to 0.1 mol/l. From the results shown in FIG. 8, it is noted that the magnitude of electrode potential of the former electrode was slightly affected by the iron aqua ion (the degree of the change of electrode potential was within 2 mV when the concentration of iron aqua ion was altered to a level ten times the original level, as indicated by line A in the figure). In the latter electrode which contained no QPVP layer, on the other hand, the magnitude of electrode potential was constant (536 mV vs. SSCE) without being affected by the iron(II) aqua ion up to its concentration of 0.1 mol/l (line B of the same figure). With both the electrodes, the response time for equilibrium potential was within five minutes.

Figure 9:
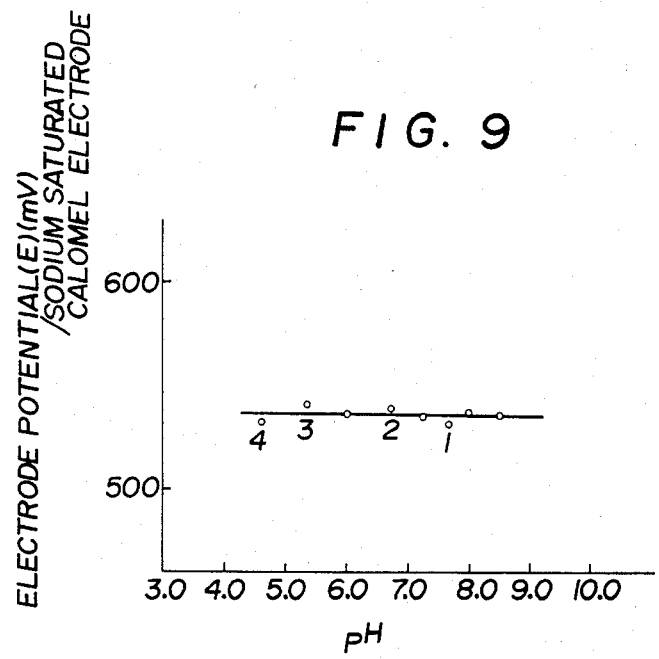

Separately in the standard serum solution (Versatol-A; general diagnostics Div. Werner-Lambert Co.) in which the hydrogen ion concentration was varied, the effect of the hydrogen ion concentration upon the value of equilibrum potential of the electrodes of this invention was examined. The results were shown in FIG. 9. It is noted from these results that the former electrode showed a constant equilibrium potential (536±2 mV vs. SSCE) in a pH range of 4.5 to 8.5 and with the latter electrode containing no QPVP layer in its construction, the value of equilibrium potential was slightly affected by hydrogen ion (not more than 7 mV/pH).

These results demonstrate that the electrodes of the present invention can be used effectively as a reference electrode in a standard serum solution.

These reference electrode of the present invention described above has the following properties and effects.

The reference electrodes of this invention can be simply constructed by depositing directly a polymer films, into which silver ions are incorporated by coordination bond, on the surface of a layer of silver or a layer of a halide on silver. Thus, these electrodes enjoy simplicity of construction. In addition, the potential response of these electrodes is rapid and the electrode potential reaches a constant value very quickly (within one minute). Further, they are not required to incorporate therein any standard solution chamber and, therefore, all allowed to undergo miniaturization to the limit imposed only by the fabricability of the conductor. Consequently, they require only a very small amount of test solution to effect a desired test. They can be used effectively as a reference electrode befitting to quick analysis.

What is claimed is:

1. A reference electrode, comprising a conductive substrate having a metallic silver surface and a layer of a silver complex polymer compound on the silver surface of said conductive substrate, wherein said silver complex polymer compound is prepared by forming a complex between a polymer compound containing a coordination nitrogen atom and a silver ion.

2. The reference electrode according to claim 1, wherein said layer of said silver complex polymer further contains a silver halide.

3. The reference electrode according to claim 2, wherein said layer comprises a mixture of said silver halide and said silver complex polymer compound containing a coordination nitrogen atom and silver ion.

4. The reference electrode according to claim 2, wherein said silver halide is silver chloride.

5. The reference electrode according to claims 1 or 2, wherein said polymer compound containing a coordination nitrogen atom is a polymer having repeating units represented by the formula I:

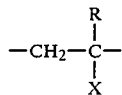

wherein R is selected from the group consisting of a hydrogen atom, an alkyl group having 1 to 6 carbon atoms and an alkoxy group having 1 to 6 carbon atoms and X is selected from the group consisting of $CONH_2$, CN and $NH_2$.

6. The reference electrode according to claim 5, wherein said polymer compound containing a coordination nitrogen atom is at least one member coordination nitrogen atom is at least one member selected from the group consisting of polyacrylamide, polymethacrylamide, polyvinylamine, polyacrylonitrile and polymethacrylonitrile.

7. The reference electrode of claim 6, wherein said polymer compound has a molecular weight of between $10^3$ and $10^6$.

8. The reference electrode according to claim 6, wherein at least the surface portion of said conductive substrate is a metallic silver.

9. The reference electrode according to claim 6, the surface portion of said conductive substrate is silver halide.

10. The reference electrode according to claim 1 or 2, wherein said layer of said silver complex polymer compound has a thickness in the range of 0.01 $\mu$m to 10 mm.

11. The reference electrode according to claims 1 or 2, further comprising a film for precluding penetration of obstructive ion species on the surface of said layer of said silver complex polymer.

12. The reference electrode according to claim 11, wherein said film for precluding penetration of an obstructive ion species is selected from the group consisting of poly(hydroxy-aromatic compounds) poly-(nitrogen-containing aromatic compounds), polypropylene, poly(organic fluorine compounds), poly(vinylidene chloride), polycarbonate, silicone, epoxy resins and polyelectrolytes.

13. The reference electrode according to claim 1 further comprising an insulating layer on the outer surface of said reference electrode.

14. The reference electrode of claim 1 further comprising a film for precluding penetration of obstructive ion species on said layer of the silver complex polymer and an insulating layer on said film for precluding penetration of obstructive ion species.

* * * * *

UNITED STATES PATENT AND TRADEMARK OFFICE
CERTIFICATE OF CORRECTION

PATENT NO. : 4,507,194

DATED : March 26, 1985

INVENTOR(S) : SHIMOMURA et al

It is certified that error appears in the above-identified patent and that said Letters Patent is hereby corrected as shown below:

Column 7, line 27, change "$\mu$in" to --$\mu$m--.

Columns 7 and 8, TABLE 1, in the column headed "Example", on the second and third lines, delete "Saran ® film"

Columns 7 and 8, TABLE 1, first line set forth under the heading "Electrode construction", change "Silver base/Ag(I)—Barex ® +/" to --Silver base/Ag(I)—Barex ® +/Saran ® film--.

Column 9, line 2, change "siler-silver" to --silver-silver--.

Column 9, last line, change "potntial" to --potential--.

UNITED STATES PATENT AND TRADEMARK OFFICE
CERTIFICATE OF CORRECTION

PATENT NO. : 4,507,194

DATED : March 26, 1985

INVENTOR(S) : SHIMOMURA et al

It is certified that error appears in the above-identified patent and that said Letters Patent is hereby corrected as shown below:

Column 11, line 37 (Claim 6), delete "coordination".

Column 12, line 1 (Claim 6), delete "nitrogen atom is at least one member".

Signed and Sealed this

Fourth Day of May, 1993

*Attest:*

MICHAEL K. KIRK

*Attesting Officer* — *Acting Commissioner of Patents and Trademarks*